United States Patent [19]

Love

[11] Patent Number: 5,645,990

[45] Date of Patent: Jul. 8, 1997

[54] IDENTIFICATION AND PATERNITY DETERMINATION BY DETECTING PRESENCE OR ABSENCE OF MULTIPLE NUCLEIC ACID SEQUENCES

[75] Inventor: Jack D. Love, Rockville, Md.

[73] Assignee: Gen Trak, Inc., Plymouth Meeting, Pa.

[21] Appl. No.: 343,738

[22] Filed: Nov. 22, 1994

Related U.S. Application Data

[63] Continuation of Ser. No. 965,537, Oct. 23, 1992, abandoned, which is a continuation of Ser. No. 598,955, Oct. 17, 1990, abandoned.

[51] Int. Cl.[6] .............................. C12Q 1/68; C07H 21/04
[52] U.S. Cl. ................................. 435/6; 536/24.31
[58] Field of Search ........................ 435/6; 536/24.31

[56] References Cited

FOREIGN PATENT DOCUMENTS

| 2206586 | 1/1989 | United Kingdom . |
| 8910977 | 11/1989 | WIPO . |

OTHER PUBLICATIONS

J.S. Beckmann, "Oligonucleotide Polymorphisms: A New Tool for Genomic Genetics", *Bio/Technology* 6 (1988) pp. 1061–1064.

M.F. Fey, "DNA fingerprints and hypervariable regions: genetic makers with numerous applications in medicine and biology", *Schweizerische Medizinische Wochenschrift* 23 (1989) pp. 815–825.

Wu et al., DNA, 8(2): 135–142 (1989).

Bogawan et al., Immunogenetics 32: 231–241 (1990).

Halmuth et al., Am. J. Hum. Genet., 47:515–523 1990.

Beckmann, Biotechnology, vol. 6, Sep. 1988, pp. 1061–1064.

Jeffreys et al., Nature, v. 332, Mar. 17, 1988, p. 278.

Gusella, Ann. Rev. Biochem., 1986, v. 55, p. 831.

*Primary Examiner*—Nancy T. Vogel
*Attorney, Agent, or Firm*—Panitch Schwarze Jacobs & Nadel, P.C.

[57] ABSTRACT

This invention relates to a process of identifying individuals or determining paternity by using Multiple Presence Polymorphic (MPP) probes. The invention also relates to Test Kits and Probes based on the process. The procedure uses multiple nucleic acid probes in separate hybridization tests, such as in different wells of a microtiter plate. The probes bind to nucleic acid sequences in some individuals, but not to others. The hybridization results convert to a unique pattern that can be used to identify an individual.

19 Claims, 3 Drawing Sheets

IDENTIFICATION AND PATERNITY DETERMINATION BY DETECTING PRESENCE OR ABSENCE OF MULTIPLE NUCLEIC ACID SEQUENCES

This application is a continuation of U.S. patent application No. 07/965,537, filed Oct. 23, 1992, now abandoned, which is a continuation of application Ser. No. 07/598,955, filed Oct. 17, 1990, now abandoned.

TECHNICAL FIELD

The present invention relates to DNA fingerprinting.

BACKGROUND OF THE INVENTION

The present invention relates to a process for producing a pattern of hybridization results that can be used to identify and distinguish human, other animal, or plant individuals. Traditionally, this type of identification is called "Nucleic Acid (DNA) Fingerprinting" or "DNA Profiling" because the uniqueness of nucleic acid banding patterns is conceptually similar to human fingerprints. The current method of DNA Fingerprinting requires the use of Southern Blotting. The method, according to the invention, is simple to perform, requires no interpretation, and provides results which convert to a simple bar code for computer storage and retrieval.

The Southern Blot

Nucleic acid hybridization has been employed as a common methodology for greater than 25 years. The current method of DNA Fingerprinting uses a modern Molecular Biology hybridization technique known as Southern Blotting[1]. The Southern blot has been a mainstay of molecular biologists since its invention in 1975. In the Southern blot method, DNA molecules must first be isolated from other cellular components by one of a variety of extraction methods. After extraction, the somewhat pure DNA is then cut with one or more restriction enzymes, generating a specific set of DNA fragments. Following DNA cutting, the fragmented DNA is separated by electrophoresis in an agarose gel. This standard technique resolves DNA fragments based on their size (molecular weight) and has greater differentiating power than other sizing procedures. Large molecules cannot pass through the matrix under the force of an electric field as readily as small molecules. Therefore, large molecules migrate more slowly. The gel resolves the DNA fragments into zones or bands of unique size.

However, the agarose gel does not provide a stable support for the subsequent hybridization reaction. Consequently, the DNA is transferred from the gel to a solid support membrane, usually composed of nylon or nitrocellulose. The DNA is transferred by either capillary action or vacuum force onto the membrane where it binds to the surface. The DNA is permanently fixed to the membrane by drying or ultraviolet light cross-linking.

The membrane is prehybridized in a special solution to block any non-specific binding sites. The membrane is then placed into a solution containing labeled, denatured probe and incubated to permit hybridization to the complementary target molecules. Many factors affect the rate, extent, and specificity of the hybridization reaction.

Hybridization is the result of complementary base pairing of single stranded nucleic acids. This binding results in formation of highly specific double stranded nucleic acid. One of the single strands typically is labeled such that it can later be measured or otherwise detected as part of a new hybrid. The hybrid molecules are generally separated from residual single stranded material, so that the hybridized label can be detected in the absence of unhybridized label. After the reaction, excess probe is washed away by a series of washing steps in detergent and dilute salt solutions.

If the probe was radioactively labeled with $^{32}p$, then autoradiography may be used to locate the position of any DNA band to which the probe bound. The membrane is simply placed next to a piece of X-ray film for several minutes to several days and then the film is developed. Wherever the radioactive particles strike the film, a dark region is formed and the target DNA can be identified. The probe may also be labeled, non-isotopically, and can be located using the appropriate detection methodology, such as fluorescence spectrophotometry, colorimetry and chemiluminescence detection.

By Southern blotting, the size of the exact fragment which bound the labeled probe is pinpointed. The Southern technique gave rise to high resolution hybridization analysis, and has formed the basis of conventional DNA Fingerprinting techniques.

Conventional DNA Fingerprinting

A conventional methodology used to show a fingerprint uses probes exhibiting restriction enzyme fragment length polymorphism (RFLP)[2,3] or allelic variation[2-4], by Southern Blot technology. These conventional polymorphic probes have target DNA fragments, which vary in length after being cut with restriction enzymes[2,3]. These polymorphic probes are either restriction fragments or minisatellites. The present invention uses probes directed at nucleic acid sequences whose presence varies in the population, referred to hereinafter as Multiple Presence Polymorphisms (MPP).

In 1985, Jeffreys[2] reported that simple tandem-repetitive regions of DNA, also known as minisatellites, showed tremendous fragment length polymorphism between human individuals. Jeffreys proposed that this probe, in combination with several restriction enzyme sets, could be used to produce a stable pattern of DNA bands unique to each individual tested. Furthermore, he proposed that the unique patterns could be applied to problems of human identification and determination of paternity.

The current method of DNA Fingerprinting using Southern Blotting has the following problems associated with it:

1. Time-consuming—requires one week or more to complete.
2. Difficult to perform—more than one hundred steps.
3. Requires highly skilled and knowledgeable technicians.
4. Not standardized—variable results from test to test and from lab to lab.
5. Inaccurate measurements—results require measurements of DNA fragment length, which varies with the particular electrophoresis conditions, temperature of buffer and environment, type of agarose gel used. Length measurement is also a highly subjective determination of the position of the DNA band.

Therefore, there is a definite need for a diagnostic or detection technique that is easy to perform, relatively fast, does not require significant expertise, and requires no subjectivity of interpretation. The present invention solves these needs by consisting of relatively few steps with only routine laboratory skills required, by being easily automatable through modification of instrumentation currently available on the market, and by providing results in about one day. Also, the results are measured in standard laboratory readers, such as an ELISA plate reader, spectrophotometer, fluorescence photometer or similar instrument. The results do not require any user interpretation; the output measurement converts to a numerical 1 (positive) or 0 (negative).

SUMMARY OF INVENTION

A plurality of novel Multiple Presence Polymorphism (MPP) probes is used in an ordered series of nucleic acid hybridization tests. The combined positive and negative results reveal a pattern. This pattern is individual specific and, therefore, is a Personal Identification Pattern (PIP). Specific nucleic acids used as MPP probes are directed against genetic polymorphisms that exhibit limited presence (or absence) in the population under examination.

SPECIFIC DESCRIPTION OF THE INVENTION

DNA Profiling by Multiple Presence Polymorphisms

Figure 1:
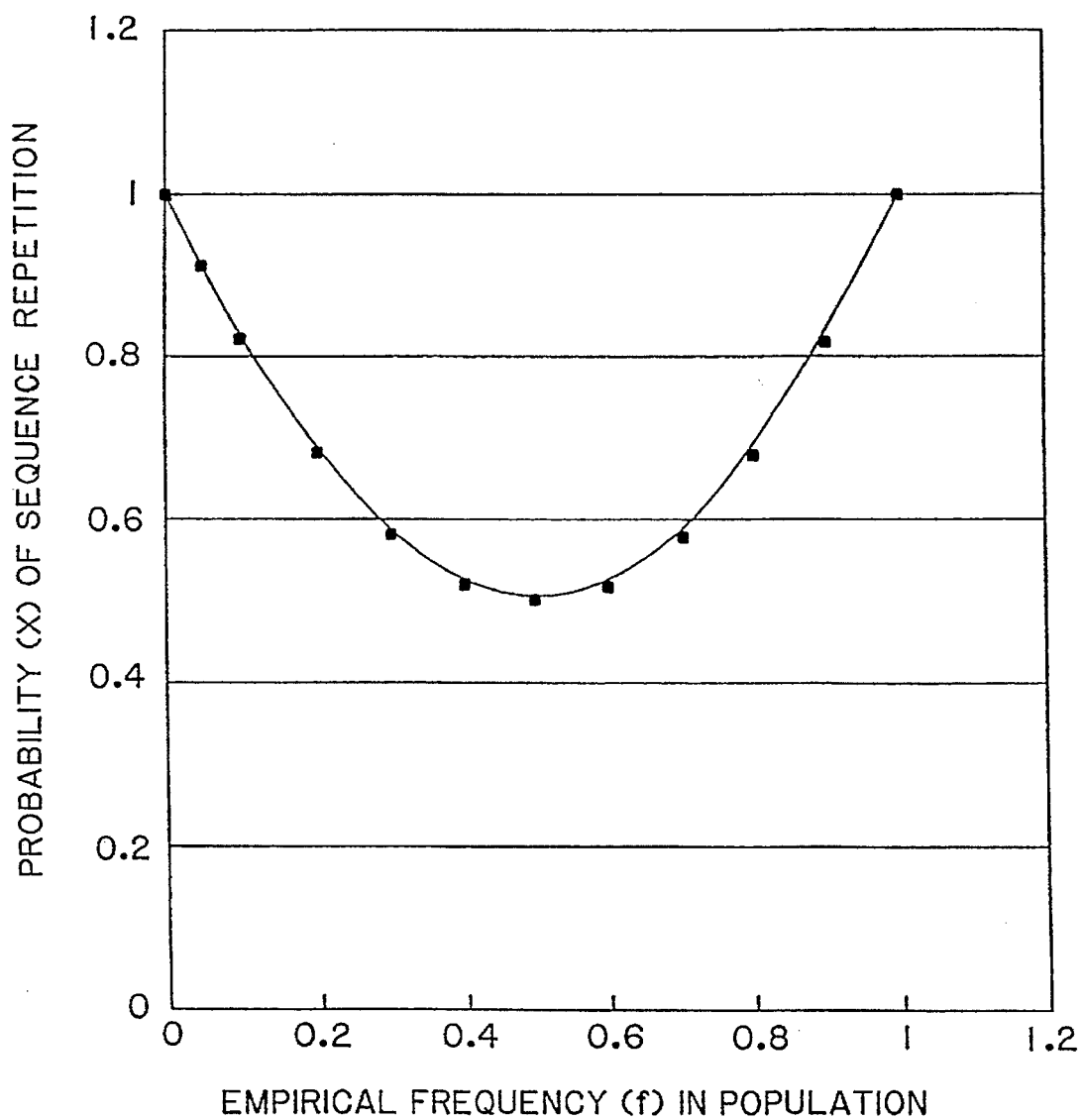
FIG. 1 Probability of Individual Sequence Repetition During the Test

The present invention avoids the use of the time-consuming and difficult to standardize and control Southern blot. The method may replace the current method of DNA Fingerprinting with one that is simple and rapid to perform, requires no interpretation, and produces results that are easy to computerize.

A new method, according to the invention, tests by nucleic acid hybridization for multiple, different nucleic acid sequences, which are polymorphic in terms of their presence in the general population, rather than in terms of fragment size. By analysis of Multiple Presence Polymorphisms (MPP), nucleic acid sequences whose presence in a population of organisms is exhibited less than 100% of the time, identity or paternity can be determined.

The test system exceeds the pattern uniqueness associated with current Southern blotting methods and is standardized for paternity or forensic purposes. Furthermore, the PIP system is far superior to complex non-standardized Southern blotting, in part because it consists of simple positive or negative results. Also, background is not significant with specimens of sufficient quantity.

This invention includes a method for identifying an individual by multiple nucleic acid hybridization tests, without the use of gel electrophoresis and the Southern blot.

The method comprises a. determining the presence of a plurality of nucleotide sequences (whole genes, fragments of genes, poly-nucleotides or oligonucleotides) within an individual, using a plurality of probes for MPPs in individual tests, each directed toward a unique nucleotide sequence, and b. hybridizing (binding) the probes to disrupted or extracted specimens from the individual, followed by separating hybridized probe and target from unbound probe (or the unhybridized label is otherwise eliminated), and c. detecting the hybrids by any suitable measuring system, where d. a positive signal indicates the presence of a particular nucleic acid sequence in the individual; and the positive and negative hybridization results, taken as a whole and ordered string, provide a unique pattern ("fingerprint") for that individual, called a Personal Identification Pattern (PIP).

After testing for the presence of each gene in a specific configuration, such as in a microtiter plate, the outcome reveals a pattern of positive or negative results. These results may be computerized as 1 (positive) or 0 (negative) and converted to a simple bar code. Thus, a pattern, easy to analyze and compare, is obtained.

The preferred nucleic acid sequences are those that exhibit polymorphism with regard to presence or absence in the general population (the population can be human, equine, murine, plant or any other organism), where the frequency of appearance of each "presence" polymorphism in the population affects the overall frequency of pattern recognition with the optimum positive sequence frequency being 50%. This is further explained in the description of MPP probes below and in FIGS. 1 and 2.

The sensitivity of detection from a typical blood specimen is sufficient to allow detection without target or signal amplification. This is ideal for routine paternity testing or establishing an individual's Personal Identification Pattern (PIP). But for forensic applications with limited specimen, the regions around the probes may be amplified by one of a variety of target amplification methods. Alternatively, the signal may be amplified to increase detection to a measurable level.

Multiple Presence Polymorphic Probes

The specific nucleic acid fragments used as probes are directed against genetic polymorphisms that exhibit limited "presence" (or absence) in the population under examination.

These are called "Presence" Polymorphisms, and the use of several of these to develop a PIP is referred to as Multiple Presence Polymorphisms (MPPs). These nucleic acid probes may be any length, such as whole genes, gene fragments, or short synthesized DNAs. In the preferred embodiment of the invention, these nucleic acid probes consist of synthesized DNA oligonucleotides and poly-nucleotides from about 10 to about 30 nucleotides long. One skilled in the art will recognize that probes of other size and/or type may also be employed.

The preferred class of candidate genes comes from RFLPs. By definition, RFLPs contain a restriction site that is polymorphic. By isolating and sequencing the region around the polymorphic enzyme site, probes are rapidly obtained that carry alterations in at least one base pair. Over 850 of these RFLPs have already been identified and most of these have had preliminary data showing the frequency of variation in the population[9]. Many hundreds of these exhibit RFLP frequencies that are useful for MPP's. Of these RFLPs, those that exhibit single bands on Southern blots are preferred MPP probes, because it is easier to determine hybridization conditions that differentiate between 100% homology and 95% or less homology.

Another group of genes from which MPP probes may be isolated are genes that exhibit a high degree of variation in the human population due to dominant and recessive traits, such as genes for brown eyes. Individuals with blue eyes completely lack the genes for brown eyes. Genetically dominant genes, like brown eyes, are good candidates for MPP probes. The reason is that in individuals lacking the particular phenotypic trait, these genes usually are completely absent. Many dominant genes of this type have been identified in the human population. Likewise, many genes on the X chromosome exhibit their phenotypes only in certain people; and, therefore, these genes are absent in all male and some female individuals lacking the trait.

It is important to avoid probes which detect acquired disease mutations such as has been done for the oncogene ras[7,8]. These probes may detect changes as these mutations occur upon development of the disease, which would result in an individual's PIP changing. On the other hand, genes that detect inherited diseases, which are based on mutations present at birth, are potential MPP probes. However, the "presence" frequency of a particular inherited disease may be too low to be useful as MPPs.

Determining the Probability of Individual Sequence Repetition in a Population

The frequency of "Presence" Polymorphism associated with the specific MPP probes may be determined for the population of organisms being evaluated by nucleic acid hybridization. The hybridization format used is not critical to the frequency of appearance in the population. Any hybridization technology, such as liquid, dot, slot, filter, capture or sandwich assay may be used to provide accurate results. The process may be performed using Southern or Northern blots, but these are not preferred. On a micro scale the process, according to the invention, is performed as an in situ hybridization test on whole cells.

Probes that detect "presence" polymorphisms are critical to MPP Analysis. Many nucleic acid sequences have potential to detect these sites. An MPP probe has a positive hybridization result in less than 100% of the individuals of a population. In the preferred embodiment of the invention, the MPP probes have a "presence" frequency in the population of 20% to 80% with the optimum probe being present in 50% of individuals. This is explained below and in FIGS. 1 and 2.

The "presence" frequency of an individual MPP probe is determined empirically by testing it in a statistically significant number of different individuals (for example 500 to 1,000). Assume that an MPP probe appeared 700 times out of 1,000 random individuals tested. The Empirical Presence Frequency (f) is 0.7 (70%). This value is used to determine the probability that a match would occur between any two individuals in a comparison of PIPs. The probability is calculated according to Equation 1.

Equation 1:
Determine the probability ($X_n$) of each probe result being repeated during the PIP test. The probability of a particular sequence being repeated during the test is defined by Equation 1, where f is the empirically determined frequency of the particular sequence in the general population.

$$(f)(f)+(1-f)(1-f)=X_1$$

Where $X_n$ is the Probability of an Individual Sequence Repeat in the general population for this particular sequence.

Example: where f=0.7

$$X_1=(0.7)(0.7)+(0.3)(0.3)=0.58$$

FIG. 1 shows the results of calculating these probabilities over the range of Empirical Presence Frequencies from 0 to 1. As is obvious, if (f) is 0 or 1, the probability of a repeat is 100%. As can be seen, the curve is symmetrical with a minimum at a frequency of 0.5. Thus, the Probability of an Individual Sequence Repeat is at a minimum when the sequence appears in the general population 50% of the time.

The Probability of an Individual Sequence Repeat is then used to determine the overall Probability of a Pattern Repeat in the population. This probability is calculated according to Equation 2.

Determining the Probability of Pattern Repetition in a Population

It is most preferred that all PIPs be statistically unique in MPP analysis. Otherwise, they would not be adequate "fingerprints". The Probability of Pattern Repetition in a population is a function of (1) the number of probes tested, in combination with (2) the Probability of Individual Sequence Repetition of each MPP probe used.

Figure 2:
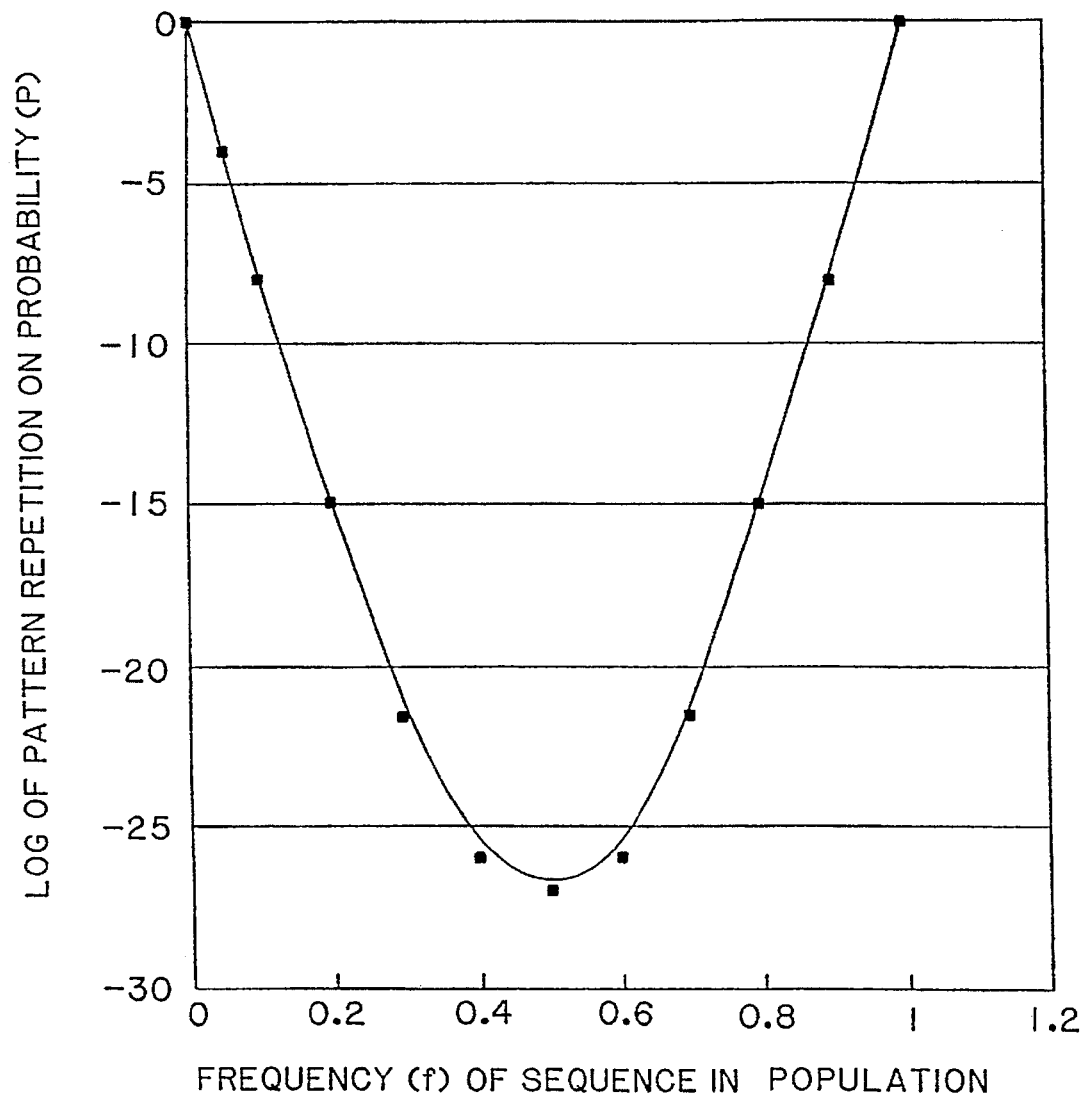
FIG. 2 Effect of Individual Presence Polymorphism on Overall Pattern Repetition Frequency FIG. 3 Conventional Microtiter Plate Configuration

The Probability of Pattern Repetition can be made far less than the entire population of the earth (about 5 billion people) by using a sufficient number of probes. Therefore, the Probability of Pattern Repetition must be less than 1 in $10^{10}$ to be functionally unique. In accordance with the invention, any number of probes may be used. For practicality sake, a sufficient number of probes is used to achieve a statistically significant level of uniqueness. As used herein, a statistically significant number can be any number depending on the user's intent, but is preferably greater than about 20 probes. Although the upper limit of probes used need not be defined, 90 probes is the current commercial limit because the preferred embodiment of MPP Analysis is in a 96-well microtiter plate. Thus, allowing 6 wells for controls, the test preferably uses up to 90 wells for MPP Analysis. The preferred embodiment comprises from 20 to 90 probes. For MPP analysis with 90 probes, the Probability of Pattern Repetition can be less than 1 in $10^{27}$, as shown in FIG. 2. This far exceeds any known application.

FIG. 2 shows the results of calculating the Probability of Pattern Repetition using Equation 2. As can be seen, this curve also has its limit at a "presence" frequency of 50% (0.5). At this presence frequency, the Probability of Pattern Repetition with 90 probes at 50% presence frequency is less than $10^{-27}$.

Equation 2:
Determine the probability of a particular set of probe tests being repeated in the population. The probability of an ordered set of results (a pattern) being repeated in the general population is the multiple of all individual sequence repeat probabilities. This is formulated by Equation 2, where $X_1, X_2, X_3$ through $X_n$ are individual sequence repeat probabilities calculated from Equation 1.

$$(X_1)(X_2)(X_3)\ldots(X_n)=P$$

Where P is the Probability of Pattern Repetition in the general population.

Example: Where all X's=0.5 and 90 sequences are analyzed. When all X's=0.5, the probability of a pattern repetition is at its minimum.

$$(0.5_1)(0.5_2)(0.5_3)\ldots(0.5_{90})=(0.5)^{90}=8\times10^{-28}$$

Kits

The Kits referred to in this invention can be used to determine both identity and paternity. Kits may contain reagents, filters, plates, and all the necessary probes to perform an analysis. All the probes are used simultaneously; but in distinct tests, such as in a microtiter plate, to produce a unique pattern of positive and negative results, which is called a Personal Identification Pattern (PIP).

One skilled in the art will recognize that the invention may comprise a kit. Kits are for detection of "presence" polymorphisms and may contain Multiple Presence Polymorphism probes, filters or plates, and reagents for processing in accordance with the invention. The test system comprises a set of nucleic acid probes (the greater the number of probes used the less the likelihood of pattern repetition), such probes being used in a manner that permits hybridizing separately to portions of the test person's nucleic acids to provide separate results for each probe test, so that by combining the test results in a predetermined, ordered sequence, such as in a microtiter plate format, the results form a pattern that is unique for the individual being tested, a PIP. The reagents include a) materials for processing, such as a) filters or plates, b) solutions for hybridizing, washing, and detection, c) specific nucleic acid probes for MPPs, and d) DNAs and probes for positive and negative controls.

Labels

Many different types of labels are used effectively with MPP probes. A good description of the many labels and their accompanying labeling methodology is contained in DNA Probes by Keller and Manak[5]. Examples of various labels include biotin or any of its derivatives, fluorophores, chemiluminescent or bioluminescent tags, digoxigenin, enzymes, mercury, haptens, bromine, DNA binding proteins, Europium-psoralen, lanthanides, modified aminos, modified nucleotides, sulfonates, AAIF, DNP, radioisotopes, or other molecules that can be subsequently detected[5]. Probes are labeled by techniques including, but not limited to nick-translation, photoaffinity labeling, random priming, direct enzyme linking, end labeling, chemical modification, tailing, transcription, direct synthesis, or conjugation[5].

Cell Lysis/Nucleic Acid Extraction

Because determination of MPPs does not require restriction enzyme digestion, the specimens do not need to be highly purified. This permits simple cell and organism disruption without nucleic acid extraction. Cells are lysed by using guanidinium thiocyanate, SDS, or other surfactants.

Nucleic Acid Capture

The crude lysates prepared as described above are used directly in the hybridization reaction with capture or sandwich assays or filtered to capture the sample nucleic acids for dot, spot, or microtiter blots. For some assays it is possible to spot directly the cells and disrupt them on the filter (filter in situ).

Blotting may be by Dot Blot or Slot Blot Manifolds, simple spot blots without the manifold, direct "filter in situ" blotting of cells, or other methods. These procedures are described in a variety of Lab Manuals and text books[1,10,11].

Hybridization Reaction

Different size probes exhibit different binding affinities. In addition, the percent homology between the probe and target affects the binding affinity. The hybridization and washing conditions chosen for MPP are able to differentiate between presence or absence of a specific nucleotide sequence or portion of that sequence used for the probe. Establishing these conditions sets the stringency. Appropriate hybridization conditions are estimated using the formulas described in Hybridization Formulas below, but final optimum conditions are empirically determined with each individual probe.

Detection/Measurement

After hybridization, the detection system used may be radioisotopic or non-isotopic such as colorimetric, fluorometric, or luminescent. The only criterion is easy detection above background. Detection methodology depends on the nature of the label used to modify the probe.

Hybridization Formulas

Equation 3:

Determining the melting point temperature ($T_m$) for DNA:DNA Hybridization using Long Probes. $T_m$ is the point at which the DNA:DNA hybrids begin to separate (denature) into single strands.

$$T_m = 81.5° C. + 16.6 \log M + 0.41 (\% G+C) - 0.7 (\% \text{Formamide})$$

Where, $M=[Na^+]$ in moles/liter

Example: for a probe of 250 bases containing 45% G+C, in 1M $Na^+$ and 50% formamide:

$$T_m = 81.5 + 16.6 \log(1) + 0.41(45) - 0.7(50)$$

$$T_m = 81.5 + (0) + 18.5 - 35 = 65° C.$$

Equation 4:

Determining the optimum hybridization temperature ($T_{hyb}$) for DNA:DNA Hybridization using Long Probes. This is the temperature at which the hybridization reaction should be performed.

$$T_{hyb} = T_m - 20° C.$$

Using the example from above gives:

$$T_{hyb} = 65° C. - 20° C. = 45° C.$$

Equation 5:

Determining the $T_m$ for short oligonucleotide probes of 14 to 40 bases. The $T_m$ formula for short probes has been empirically determined; it is a function of the relative base pair content of the probe and target. Standard sodium ion concentration without formamide are the reaction conditions used.

$$T_m = 4° C. \text{ per GC pair} + 2° C. \text{ per AT pair}$$

Example: using a 20-mer with a GC content of 50%, the $T_m$ would be determined as follows:

$$T_m = 4° C.(10) + 2° C.(10) = 60° C.$$

Equation 6:

Determining the $T_{hyb}$ for short oliqonucleotide probes.

$$T_{hyb} = T_m - 5° C.$$

Therefore, $T_{hyb}$ for the above 20-mer would be 55° C.

EXAMPLE 1.

The following is an example using DNA hybridization in a Microtiter Dot Blot format. Many of the specific steps referred to in Example 1 are found in many laboratory manuals such as Maniatis et al.

Specimen for Human DNA Profiling

Blood, semen, tissue, or any specimen containing nucleic acids will be used. Cells will be disrupted to liberate the nucleic acids in a medium that prevents their breakdown. The nucleic acids may or may not be extracted, depending on the requirements of the specimen or organism.

Nucleic Acid Extraction: From whole blood

1. Collect blood specimen in EDTA anticoagulant.
2. Centrifuge blood at 400×g for 5 minutes at room temperature to separate the red cells from the white cells. The white cells will form a layer on top of the red cells. Carefully remove the white cell layer with a Pasteur pipette and place into a new polypropylene test tube.
3. Resuspend cells and add Lysis Buffer (20 mM Tris-HCl, pH 7.5; 20 mM NaCl; 20 mM EDTA) to bring the total volume to 2 ml. Lyse cells by adding 0.1 ml of 10% SDS.
4. Add 0.2 ml of 20 mg/ml Proteinase K. Incubate at 50° C. for 1 hour to digest proteins.
5. Extract nucleic acids by adding an equal volume (2.3 ml) of PCI (phenol:chloroform:isoamyl alcohol; 25:24:1) and vortexing vigorously for 1 minute. Centrifuge for 10 minutes to separate the two phases.

6. Transfer the upper, aqueous layer to a new tube. Extract again with an equal volume of PCI.
7. Again transfer the upper, aqueous layer to a new tube. Add an equal volume of chloroform:isoamyl alcohol (24:1) and vortex for 1 minute. Centrifuge for 10 minutes.
8. Transfer the aqueous layer to a new tube. Add 1/10 volume (0.2 ml) of 2M Na Acetate, pH 5.0 and 2 volumes of ice cold 100% ethanol. Incubate at −20° C. for at least 1 hour. Centrifuge for 10 minutes in a microfuge.
9. Carefully remove the ethanol from the tube leaving the DNA pellet. Wash the pellet by adding 2 ml of cold 70% ethanol and gently vortexing. Centrifuge for 10 minutes in a microfuge.
10. Carefully remove the ethanol and drain the excess ethanol by inverting the tube onto a paper towel or by drying under vacuum. Do not allow the pellet to become completely dry or it will be difficult to redissolve.
11. Dissolve the DNA/RNA in 0.5 ml of 10 mM Tris-HCl, pH 7.5, 1 mM EDTA.

OPTIONAL REMOVAL OF RNA STEPS 12–16

Depending on the application, RNA may have positive or negative benefits. Therefore, this procedure will be performed to remove the RNA when necessary. Removal of RNA may be necessary if the MPP probes cross react to ribosomal RNA or some other RNA resulting in background.

12. Add RNase A to a final concentration of 100 ug/ml and incubate at 37° C. for 30 to 60 minutes.
13. Add SDS to a final concentration of 0.5% and Proteinase K to a final concentration of 100 ug/ml. Incubate at 37° C. for 30 to 60 minutes.
14. Extract the solution with PCI as in steps 4 and 5.
15. Extract the solution with Chloroform as in step 7.
16. Precipitate, wash, and redissolve the DNA as in steps 8–11.
17. Store the DNA solution at −20° C.

Blotting the Nucleic Acids on a Membrane

The individual's DNA sample will be split into multiple different parts (up to 90 depending on the number of individual probe tests to be performed). The specimens will be blotted onto a membrane filter to prepare for hybridization with multiple different probes.

The preferred method to perform the blotting is in a Microtiter Dot Blot format using a Millipore microtiter plate with a nylon membrane attached to the bottom of the wells (or the equivalent from other manufacturers). This type of plate will permit filtering, hybridizing with different probes in each well, and washing of samples without interference (cross contamination or bleeding) from other wells.

18. Assemble a Vacuum Plenum apparatus suitable for use with the microtiter filter plate (any of the commercially available 96-well Vacuum Plenums will suffice ).
19. Place the microtiter filter (nylon) plate into the plenum. Wet the membrane with 0.5M NaOH by adding 0.2 ml to each well.
20. Remove a sample of the individual's nucleic acid solution and denature by adding 10M NaOH to a final concentration of 0.5M. If RNA is in the sample, continue to step 21 without delay or the RNA will be destroyed.
21. Add 200 ul of the denatured nucleic acid solution to each well being tested.
22. Apply a vacuum to the manifold to suck the contents of the wells through the porous membrane. The nucleic acids will bind to the membrane.

OPTIONAL STEP FOR USE WITH RNA CONTAINING SAMPLES STEP 23

23. Add 200 ul of 1M Tris-HCl, pH 7.0 and filter as in step 22.
24. After the samples have been completely removed from the wells, disassemble the apparatus and bake the membrane at 60° C. for 30 minutes or air dry completely.

Labeled Probes

The probes will be composed of either DNA or RNA. The probe labeling methodology used will depend on the type of label employed. The only requirement for the label is definitive detectability above background. The preferred label will yield a color change on the filter that can be easily measured in a standard ELISA reader. For example, biotinylated probes will be suitable for this type of detection system. For labeling oligonucleotides, chemical attachment[5] or photo-biotinylation[5] yields the best probe.

Hybridization Reaction

The oligonucleotide probe, containing a label that will be subsequently detected, will be added to the medium containing the target (individual's) nucleic acids. The solution will be incubated at appropriate hybridization conditions, including salt, formamide, temperature and time to allow the probe and target to combine (hybridize).

The preferred Prehybridization Solution for working with nylon membranes will contain the following chemicals:

| | |
|---|---|
| 0.1 mg/ml | Yeast tRNA (sonicated herring sperm DNA may be substituted if filtration to remove reagents is not used for subsequent steps) |
| 0.2% | Ficoll |
| 0.2% | Bovine Serum Albumin (or Glycine) |
| 0.2% | Polyvinyl Pyrollidone |
| 6X | SSC (sodium chloride, sodium citrate) |
| 1% | SDS (sodium dodecyl sulfate) |

25. Prehybridize all wells of the membrane with the appropriate Prehybridization Solution to block non-specific binding of the probes. In the preferred procedure, the Prehybridization Solution is the same as in the hybridization for each probe. Prehybridize at 37° C. for 30 to 60 minutes.
26. Following prehybridization, remove the excess solution by filtering under vacuum or by pouring out the solution.
27. Rinse the wells one time with 6X SSC, and filter to remove excess reagent.

In the Microtiter Dot Blot format, it is preferred that the temperature used for hybridization and washing be the same for all wells. This will make processing much easier. The stringency of the reaction, which will set the desired probe specificity (or percent homology), will be controlled by the salt or formamide concentration. (See Hybridization Formulas above for detailed equations showing how to determine the appropriate hybridization conditions.)

The hybridization conditions will be able to differentiate between oligonucleotides of 20 base pairs with 100% homology to the target nucleic acid sequence from targets exhibiting 95% homology or less. The approximate reaction conditions for this degree of distinction with 20-mers is shown in the following example.

The preferred Hybridization Solution for working with nylon membranes will contain the following chemicals:

| | |
|---|---|
| 0.1 mg/ml | Yeast tRNA (Sonicated Herring Sperm DNA may be substituted if filtration to remove reagents is not used in subsequent steps) |
| 0.2% | Ficoll |

| | |
|---|---|
| 0.2% | Bovine Serum Albumin (or Glycine) |
| 0.2% | Polyvinyl Pyrollidone |
| 6X | SSPE |
| 1% | SDS (sodium dodecyl sulfate) |
| Optional | Formamide (50%) |
| Optional | Dextran Sulfate (5–10%) |

There are many variations of this basic reagent. The final concentration of these reagents will depend upon the membrane material (nylon, nitrocellulose, or paper), the length and GC content of the probes, and the type of label used (eg. radioisotope, biotin, luminescent, etc.).

28. Prepare probe solution by mixing each labeled probe (30 to 90 different solutions will be prepared) into the Hybridization Solution to the appropriate final concentration (the final concentration depends on the nature of the label). For biotinylated probes use 0.1 to 0.2 mg/ml in the Hybridization Solution.

29. Place 0.2 ml of Probe Solution 1 into Well 1, 0.2 ml of Probe Solution 2 into Well 2, and continue until all Probe Solutions have been added.

30. Incubate at the appropriate temperature for the specific probe length and Hybridization Solution used. For a biotinylated 20-mer with a 50% GC content in the Hybridization Solution described above without formamide or dextran sulfate, the $T_{hyb}$ will be about 55° C. (see Hybridization Formulas above for calculations).

31. Hybridize for 16 hours at 55° C.

Washing

Excess, unbound probe will be eliminated by physical separation or by another means, such as chemical degradation, to destroy unbound probe. Remaining probe, which will be hybridized to its specific, complementary sequence, will be detected.

32. Remove the excess Hybridization Solution by pouring out the solution.

33. Rinse each well three times with Wash Solution 1 (0.2 ml of 0.1X SSC, 1% SDS) at room temperature to remove unbound, excess probe. The Wash Solution concentrations may be varied to accommodate different probes at the same washing temperature.

34. For the final high stringency wash, add 0.2 ml of Wash Solution to each well and incubate at 55° C. for 30 minutes to remove mismatched probe. Filter or pour off the excess wash solution. Repeat this wash one time.

Detection

Detection methodology will depend on the nature of the label used to modify the probe. A typical method for developing biotinylated probe signal is described below. It is important not to let the membrane completely dry between any of these steps. All incubations will be at room temperature.

35. To each well add 0.2 ml of Blocking Solution 1 (3% BSA in 50 mM Tris-HCl, pH 7.4, 20 mM NaCl, 0.3% Tween-20, 0.01% Thimerosal) and incubate for 15 minutes.

36. Filter or pour off the excess Blocking Solution. To each well add 0.2 ml of Enzyme Conjugate solution (1 ug/ml alkaline phosphatase-streptavidin conjugate in Blocking Solution) and incubate for 10 minutes.

37. Filter or pour off Enzyme Conjugate Solution. Wash each well 3 times in 0.2 ml of Washing Solution 2 (50 mM Tris-HCl, pH 7.4, 20 mM NaCl, 0.3% Tween-20, 0.01% Thimerosal) for 5 minutes each. Filter or pour off Washing Solution 2 between each wash.

38. Add 0.2 ml of Substrate Solution (NBT/BCIP) to each well and incubate for 15 minutes to 2 hours in the dark until color develops.

39. Stop development by washing each well in deionized water. Dry the wells on filter paper.

EXAMPLE 2

This technique will substitute tetramethylammonium chloride (or tetraethylammonium chloride) for sodium chloride in the Hybridization Solution[6]. All other steps will be the same as in Example 1. This salt change avoids the effects of relative % GC content on the stability of hybrids formed. This will be useful for preparing MPP probes because the oligonucleotide sequences do not need similar % GC content to perform similarly in the hybridization reaction. The reagent system will be much simpler. This alternative method has been previously applied to the analysis of ras gene mutations in human colorectal cancers[7,8].

Hybridization Reaction

As in Example 1, the biotinylated oligonucleotide probe will be added to the medium containing the target (individual's) nucleic acids. The solution will be incubated at appropriate hybridization conditions, including the Hybridization Solution described below. The temperature and time to allow the probe and target to combine (hybridize) are discussed below.

The preferred Prehybridization Solution for working with nylon membranes will contain the following chemicals:

| | |
|---|---|
| 0.1 mg/ml | Yeast tRNA (sonicated herring sperm DNA may be substituted if filtration to remove reagents is not used for subsequent steps) |
| 0.2% | Ficoll |
| 0.2% | Bovine Serum Albumin (or Glycine) |
| 0.2% | Polyvinyl Pyrollidone |
| 3 M | Tetramethylammonium Chloride |
| 50 mM | Tris-HCl, pH 8.0 |
| 2 mM | EDTA |
| 1% | SDS (sodium dodecyl sulfate) |

25. Prehybridize all wells of the membrane with the appropriate Prehybridization Solution to block non-specific binding of the probes. In the preferred procedure, the Prehybridization Solution is the same as is used during hybridization for each probe. Prehybridize at 56° C. for 30 to 60 minutes.

26. Following prehybridization, remove the excess solution by filtering under vacuum or by pouring out the solution.

The hybridization conditions have been determined to differentiate between oligonucleotides of 20 base pairs with 100% homology to the target nucleic acid sequence from targets exhibiting a single base pair mismatch. Although the exact reaction conditions will be determined empirically, the approximate reaction conditions for this degree of distinction with 20-mers are shown in the following example.

27. Prepare probe solution by mixing each labeled probe (30 to 90 different solutions will be prepared) into the Hybridization Solution to the appropriate final concentration (the final concentration depends on the nature of the label). For biotinylated probes use 0.1 to 0.2 mg/ml in the Hybridization Solution.

28. Place 0.2 ml of Probe Solution 1 into Well 1, 0.2 ml of Probe Solution 2 into Well 2, and continue until all Probe Solutions have been added.

29. Incubate at the appropriate temperature for the specific probe length and Hybridization Solution used. The $T_{hyb}$ will be about 56° C. (see Hybridization Formulas above for calculations).

30. Hybridize for 1 to 16 hours at 56° C.

Washing

Excess, unbound probe will be eliminated by physical separation or by another means, such as chemical degradation, to destroy unbound probe. Remaining probe, which will have hybridized to its specific, complementary sequence, will be detected.

31. Remove the excess Hybridization Solution by pouring out the solution.
32. Rinse each well three times with Wash Solution 1 (0.2 ml of 2X SSPE, 1% SDS) for about 5 minutes at room temperature to remove unbound, excess probe. The Wash Solution concentrations may be varied to accommodate different probes at the same washing temperature.
33. For the final high stringency wash, add 0.2 ml of High Salt Wash Solution (5X SSPE, 1.0% SDS) to each well and incubate at 59° C. to 73° C. (depending on the probe) for 5 minutes to remove mismatched probe. Filter or pour off the excess wash solution.
34. Wash filters twice in Hybridization Solution without 0.2% Ficoll, 0.2% Bovine Serum Albumin (or Glycine), 0.2% Polyvinyl Pyrollidone, or Yeast tRNA(or DNA) for 1 hour at 59° C. to 60° C.

Results of Examples 1 or 2

Positive results will be indicated by a signal that can be discriminated above background (negative control). With biotinylated probes and alkaline phosphatase conjugates, the signal will be purplish-blue.

Figure 3:
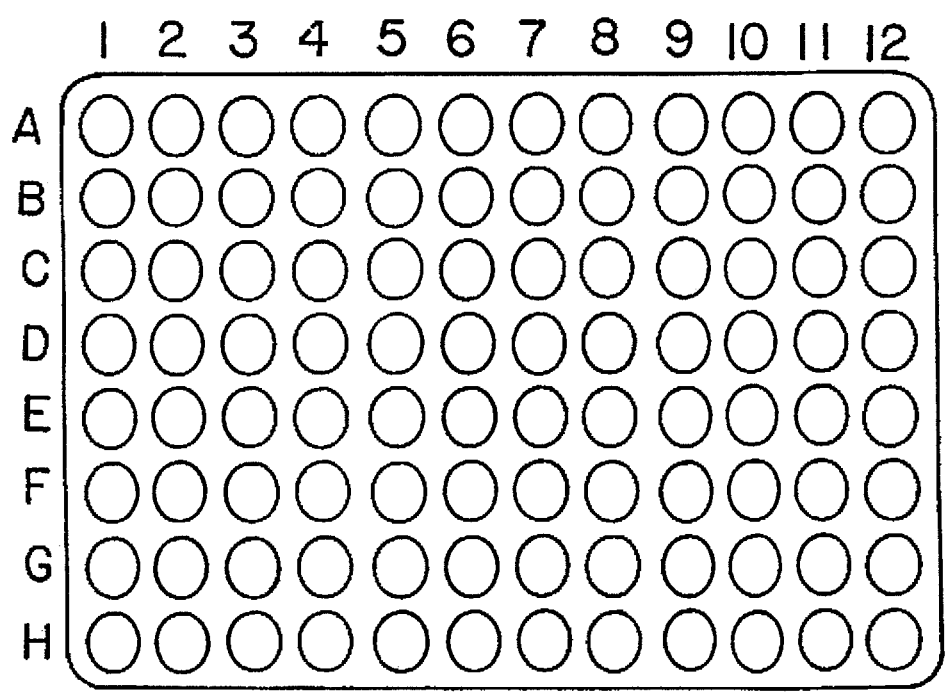

Positive results will be scored as a 1, and negative results will be scored as a 0. Results will be entered into a computer program according to a previously determined configuration for comparison to other patterns. A typical microtiter plate pattern is shown in FIG. 3.

Analysis of Results a. For Individual Identification

A single individual will exhibit a stable pattern of positive and negative results with a specific probe set (for practical reasons in a microtiter plate, this will be up to 90 MPP probes). This individual will give the same pattern in any analysis. Therefore, comparison to previous results will always reveal the identical pattern for the same set of gene fragments. All common specimens taken from separate tissues of the same individual will exhibit the same pattern. The exception will be identical twins. No two non-identical individuals will have the same pattern if sufficient number of MPP probes is used to achieve a level of uniqueness of less than 1 in $10^{10}$. Using MPP probes with a presence frequency of 0.5, only 33 probes are required, according to Equation 2. Using probes with a "presence" frequency of 0.2, 60 probes are required for a 1 in $10^{10}$ level of uniqueness. Thus, the "presence" frequency combined with the number probes used determine the PIP uniqueness.

Probes to the HLA DQ-alpha locus have been used to assist in ruling out murder suspects. In some cases, specimens such as hair from the victim and from the crime scene can be tested to see if they exhibit different HLA DQ-alpha alleles. There are 6 distinguishable forms of this locus. Comparisons are made of the HLA DQ-alpha genetic makeup of the suspect, victim, and assailant. This information can be used to rule out some suspects, but cannot be used to identify a suspect with much accuracy. The range of probabilities for identity due to chance using information from the HLA DQ-alpha locus is between 1 in 10 and 1 in 100. MPP Analysis can have better accuracy by up to 25 orders of magnitude, and is likely to be used to rule in potential suspects!

Also, care is taken to avoid MPP probes that detect mutagenic diseases, such as in cancerous cells that may alter certain of their genes during the individual's lifetime. This alteration would result in a change to the individual's PIP.

For PIPs, the number of MPP probes used is a function of the Probability of Individual Sequence Repetition of each probe, and the Probability of Pattern Repetition needed by the user, as described above in Specific Description of the Invention. For practical reasons using a microtiter plate format, the number of MPP probes used is 90 or less. One important use of PIPs is to identify persons from blood, sperm or other tissue samples by matching unknowns with specimens taken from the suspect individual.

b. For Paternity

Similar to PIPs, the number of MPP probes used for paternity determination is a function of the Probability of Individual Sequence Repetition of each probe, and the Probability of Pattern Repetition needed to establish the relationship.

Comparison of patterns between the mother and child will reveal differences in results of specific genes. Comparison of these different genes with the presumptive father will show whether these genes came from the father. A potential match will be achieved when the father contributes all the genes that are different from the mother.

In some cases the number of child's genes which differ from the mother may be only a few. This has the effect of increasing the number of potential fathers who could have a perfect match. Therefore, it is desirable to determine the probability that a match is unique. The probability that the putative father is the real father is determined from a combination of frequencies of the child's genes that differ from the mother.

If the number of gene variations from the mother is sufficient, then a probability will be determined that the presumptive father is indeed the father. The required exclusion frequency is probably no more than 1 in $10^5$. Using MPPs with a Presence Frequency of 50%, this exclusion frequency requires 16 probe differences between the mother and child, according to Equation 2.

References

1. Southern, E M (1975) J Mol Biol 98: 503
2. Jeffreys, A. J., Wilson V, and Thein, S. L. (1985) Nature 316(4): 76–79.
3. Jeffreys, A. J., Wilson, V, Thein, S. L. (1985) Nature 314(7): 67–73.
4. Jeffreys, A. J., Wilson, V, Thein, S. L., Weatherall, D. J., and Ponder, B. A. J. (1986) Amer J Human Genetics 39: 11–24.
5. *DNA Probes* (1989) eds. Keller, G. H. and Manak, M. M., Macmillan Publishers Ltd, Great Britain.
6. Melchior, W. B., and Von Hippel, P. H. (1973) Proc. Nat. Acad. Sci. USA 70(20): 298–302.
7. Verlaan-de Vries, M, Bogaard, M. E., van den Elst, H, van Boom, J. H., van der Eb, A. J., and Bos, J. L. (1986) Gene 50: 313–320.
8. Bos, J. L., Fearon, E. R., Hamilton, S. R., Verlaan-de Vries, M, van Boom, J. H., van der Eb., A. J., And Vogelstein, B (1987) Nature 327: 293–297.
9. Willard, H, et al (1985) Cytogenetics and Cell Genetics 40: 360–489.
10. *Molecular Cloning, A Laboratory Manual* (1982) Eds. Maniatis, T, Fritsch, E. F., and Sambrook, J., Cold Spring Harbor Laboratory.
11. *Nucleic Acid Hybridization, A Practical Approach* (1985) Eds. Hames, B. D. and Higins, S. J., IRL Press, Washington DC.

I claim:

1. A kit comprising:

a plurality of nucleic acid probes, each having a limited presence polymorphism, wherein the nucleic acid probes are complementary to nucleotide sequences present in individual organisms in a population of the organisms which includes a test subject organism, and wherein the nucleic acid probes each provides positive hybridizations occurring at a frequency of about 10% to about 90% in the organism population, wherein the plurality of nucleic acid probes is of a number whose hybridization signals, when combined, represent a polymorphic pattern sufficient to determine individuality of the test subject organism in the organism population and wherein the number of probes is sufficient to result in a probability (P) of hybridization signal pattern repetition in the organism population of less than $1 \times 10^{-5}$, where P is the product of individual sequence repeat probabilities for each nucleotide sequence region probed with the labeled nucleic acid probes, each individual sequence repeat probability (X) being calculated as $$X = \left( \frac{\text{percentage presence frequency}}{100} \right)^2 + \left( 1 - \frac{\text{percentage presence frequency}}{100} \right)^2 ;$$

and a suitable container.

2. The kit of claim 1 further comprising at least one of the following:

a filter;

a microtiter plate;

a hybridizing reagent;

a washing reagent;

a detection or labeling reagent; and nucleotide sequences for positive and negative controls.

3. The kit of claim 1 wherein the number of nucleic acid probes is at least 16.

4. The kit of claim 1 wherein the number of nucleic acid probes is at least 20.

5. A method for determining individuality of an organism in a population of the organism comprising:

a) obtaining a plurality of nucleic acid sequences from the organism;

b) hybridizing an aliquot of the nucleic acid sequences to a labeled nucleic acid probe, wherein the nucleic acid probe is complementary to a region of at least one nucleic acid sequence, the region having a presence frequency in the organism population of about 10 percent to about 90 percent;

c) detecting a positive or negative hybridization signal which signals a respective presence or absence of hybridization of a nucleic acid sequence in the aliquot to the labeled nucleic acid probe;

d) repeating steps b) and c) with different labeled nucleic acid probes to achieve a pattern of positive or negative hybridization signals wherein the number of repetitions of steps b) and c) is that which results in a probability (P) of hybridization signal pattern repetition in the organism population of less than $1 \times 10^{-5}$, where P is the product of individual sequence repeat probabilities for each nucleic acid sequence region probed with the labeled nucleic acid probes, each individual sequence repeat probability (X) being calculated as $$X = \left( \frac{\text{percentage presence frequency}}{100} \right)^2 + \left( 1 - \frac{\text{percentage presence frequency}}{100} \right)^2 .$$

6. The method of claim 5 wherein the presence frequency is about 20 percent to about 80 percent.

7. The method of claim 6 wherein the presence frequency is about 50 percent.

8. The method of claim 7 wherein the number of repetitions of steps b) and c) is at least 15, for a total number of different probes of at least 16.

9. The method of claim 5 wherein the labeled nucleic acid probe comprises a nucleotide sequence having a limited presence polymorphism.

10. The method of claim 9 wherein the limited presence polymorphism is a restriction fragment length polymorphism.

11. The method of claim 5 wherein the nucleic acid probe is a whole gene, a gene fragment or an oligonucleotide.

12. The method of claim 11 wherein the nucleic acid probe is an oligonucleotide of about 10 to about 30 nucleotides.

13. The method of claim 5 wherein steps b) and c) are repeated about 19 to about 89 times.

14. The method of claim 5 wherein the probability (P) of hybridization signal pattern repetition in the organism population is less than $1 \times 10^{-10}$.

15. The method of claim 5 wherein the nucleic acid sequences are genomic DNA that has not been size separated.

16. The method of claim 15 wherein the genomic DNA is undigested DNA.

17. A method for determining paternity comprising:

(i) performing the method of claim 5 with nucleic acid sequences from a maternal organism, the maternal organism's offspring and a putative paternal organism;

(ii) comparing the patterns of negative and positive hybridization signals achieved from the maternal organism and the maternal organism's offspring to determine the differences between the two patterns; and (iii) comparing the pattern of negative and positive hybridization signals achieved from the putative paternal organism with the differences determined in comparing step (ii), whereby the putative paternal organism is determined to be the paternal organism when the differences are substantially accounted for by the paternal pattern.

18. The method of claim 17 wherein the nucleic acid sequences are genomic DNA that has not been size separated.

19. The method of claim 18 wherein the genomic DNA is undigested DNA.

* * * * *